United States Patent
Wu et al.

(10) Patent No.: US 7,335,314 B2
(45) Date of Patent: *Feb. 26, 2008

(54) METHOD OF MAKING AN IMPLANTABLE MEDICAL DEVICE

(75) Inventors: Steven Z. Wu, Santa Clara, CA (US); Sameer Harish, Fremont, CA (US); Deborra Sanders-Millare, San Jose, CA (US); Judy A. Guruwaiya, San Jose, CA (US); Daryush Mirzaee, Sunnyvale, CA (US); Syed Hossainy, Fremont, CA (US); Charlene Chen, Redondo Beach, CA (US)

(73) Assignee: Advanced Cardiovascular Systems Inc., Santa Clara, CA (US)

( * ) Notice: Subject to any disclaimer, the term of this patent is extended or adjusted under 35 U.S.C. 154(b) by 328 days.

This patent is subject to a terminal disclaimer.

(21) Appl. No.: 10/912,025

(22) Filed: Aug. 4, 2004

(65) Prior Publication Data
US 2005/0033412 A1 Feb. 10, 2005

Related U.S. Application Data

(62) Division of application No. 09/675,092, filed on Sep. 28, 2000, now Pat. No. 6,805,898.

(51) Int. Cl.
*B44C 1/22* (2006.01)
*B32B 1/08* (2006.01)
*C25F 3/00* (2006.01)
*A61F 2/06* (2006.01)

(52) U.S. Cl. .................. 216/10; 216/11; 623/1.15; 623/1.42

(58) Field of Classification Search .............. 216/10, 216/11; 623/1.4, 1.42, 1.43, 1.15
See application file for complete search history.

(56) References Cited

U.S. PATENT DOCUMENTS 3,586,999 A 6/1971 Southgate (Continued)

FOREIGN PATENT DOCUMENTS

EP 0 687 008 12/1995

(Continued)

OTHER PUBLICATIONS

Barath et al., *Low Dose of Antitumor Agents Prevents Smooth Muscle Cell Proliferation After Endothelial Injury*, JACC 13(2):252A (Abstract) (1989).

(Continued)

*Primary Examiner*—Roberts Culbert
(74) *Attorney, Agent, or Firm*—Squire Sanders & Dempsey, LLP

(57) ABSTRACT

An implantable medical device, such as a stent or graft, having asperities on a designated region of its outer surface is disclosed. The asperities can serve to improve retention of one or more layers of a coating on the device and to increase the amount of coating that can be carried by the device. The asperities can be formed by using a stream of pressurized grit to roughen the surface. The asperities can also be formed by removing material from the outer surface, for example, by chemical etching with or without a patterned mask. Alternatively, the asperities can be formed by adding material to the outer surface, for example, by welding powder particles to the outer surface or sputtering.

17 Claims, 7 Drawing Sheets

U.S. PATENT DOCUMENTS

| | | | |
|---|---|---|---|
| 3,855,638 A | 12/1974 | Pilliar | |
| 4,006,270 A | 2/1977 | Morgan | |
| 4,101,984 A | 7/1978 | MacGregor | |
| 4,321,711 A | 3/1982 | Mano | |
| 4,355,426 A | 10/1982 | MacGregor | |
| 4,374,669 A | 2/1983 | MacGregor | |
| 4,459,252 A | 7/1984 | MacGregor | |
| 4,693,721 A | 9/1987 | Ducheyne | |
| 4,729,871 A | 3/1988 | Morimoto | |
| 4,733,665 A | 3/1988 | Palmaz | |
| 4,800,882 A | 1/1989 | Gianturco | |
| 4,886,062 A | 12/1989 | Wiktor | |
| 5,059,211 A | 10/1991 | Stack et al. | |
| 5,163,952 A | 11/1992 | Froix | |
| 5,163,958 A | 11/1992 | Pinchuk | |
| 5,234,456 A | 8/1993 | Silvestini | |
| 5,306,286 A | 4/1994 | Stack et al. | |
| 5,328,471 A | 7/1994 | Slepian | |
| 5,370,682 A | 12/1994 | Schmitt | |
| 5,370,684 A | 12/1994 | Vallana et al. | |
| 5,419,760 A | 5/1995 | Narciso, Jr. | |
| 5,433,909 A | 7/1995 | Martakos et al. | |
| 5,437,834 A | 8/1995 | Okimatsu et al. | |
| 5,441,515 A | 8/1995 | Khosravi et al. | |
| 5,443,500 A | 8/1995 | Sigwart | |
| 5,464,650 A | 11/1995 | Berg et al. | |
| 5,492,768 A | 2/1996 | Okimatsu et al. | |
| 5,507,815 A * | 4/1996 | Wagner et al. | 623/23.5 |
| 5,514,154 A | 5/1996 | Lau et al. | |
| 5,522,894 A | 6/1996 | Draenert | |
| 5,527,337 A | 6/1996 | Stack et al. | |
| 5,569,295 A | 10/1996 | Lam | |
| 5,571,187 A | 11/1996 | Devanathan | |
| 5,605,693 A | 2/1997 | Seare, Jr. | |
| 5,605,696 A | 2/1997 | Eury et al. | |
| 5,607,463 A | 3/1997 | Schwartz et al. | |
| 5,624,411 A | 4/1997 | Tuch | |
| 5,630,840 A | 5/1997 | Mayer | |
| 5,632,779 A | 5/1997 | Davidson | |
| 5,697,967 A | 12/1997 | Dinh et al. | |
| 5,700,286 A | 12/1997 | Tartaglia | |
| 5,707,385 A | 1/1998 | Williams | |
| 5,713,949 A | 2/1998 | Jayaraman | |
| 5,725,567 A | 3/1998 | Wolff et al. | |
| 5,741,429 A | 4/1998 | Donadio et al. | |
| 5,746,691 A | 5/1998 | Frantzen | |
| 5,749,880 A | 5/1998 | Banas et al. | |
| 5,755,771 A | 5/1998 | Penn et al. | |
| 5,759,192 A | 6/1998 | Saunders | |
| 5,766,238 A | 6/1998 | Lau et al. | |
| 5,766,710 A | 6/1998 | Turnlund et al. | |
| 5,769,883 A | 6/1998 | Buscemi et al. | |
| 5,788,558 A | 8/1998 | Klein | |
| 5,800,512 A | 9/1998 | Lentz et al. | |
| 5,824,455 A | 10/1998 | Komatsu et al. | |
| 5,843,172 A | 12/1998 | Yan | |
| 5,856,814 A | 1/1999 | Yagyu | |
| 5,873,904 A | 2/1999 | Ragheb et al. | |
| 5,879,398 A | 3/1999 | Swarts et al. | |
| 5,902,266 A | 5/1999 | Leone et al. | |
| 5,916,234 A | 6/1999 | Lam | |
| 5,928,279 A | 7/1999 | Shannon et al. | |
| 5,945,029 A | 8/1999 | Scholz et al. | |
| 5,951,881 A | 9/1999 | Rogers et al. | |
| 5,972,027 A | 10/1999 | Johnson | |
| 6,008,431 A * | 12/1999 | Caldarise et al. | 623/23.3 |
| 6,010,529 A | 1/2000 | Herweck et al. | |
| 6,027,779 A | 2/2000 | Campbell et al. | |
| 6,033,582 A | 3/2000 | Lee et al. | |
| 6,071,296 A * | 6/2000 | Lashinski et al. | 606/194 |
| 6,095,817 A | 8/2000 | Wagner et al. | |
| 6,099,561 A * | 8/2000 | Alt | 623/1.44 |
| 6,120,536 A | 9/2000 | Ding et al. | |
| 6,120,847 A | 9/2000 | Yang et al. | |
| 6,143,370 A | 11/2000 | Panagiotou et al. | |
| 6,165,210 A | 12/2000 | Lau et al. | |
| 6,203,732 B1 | 3/2001 | Clubb et al. | |
| 6,206,915 B1 | 3/2001 | Fagan et al. | |
| 6,240,616 B1 | 6/2001 | Yan | |
| 6,273,913 B1 | 8/2001 | Wright et al. | |
| 6,287,337 B1 | 9/2001 | Martakos et al. | |
| 6,287,628 B1 | 9/2001 | Hossainy et al. | |
| 6,312,459 B1 | 11/2001 | Huang | |
| 6,379,381 B1 | 4/2002 | Hossainy et al. | |
| 6,395,326 B1 | 5/2002 | Castro et al. | |
| 6,558,733 B1 | 5/2003 | Hossainy et al. | |
| 6,610,087 B1 | 8/2003 | Zarbatany et al. | |
| 6,783,543 B2 | 8/2004 | Jang | |
| 6,805,898 B1 * | 10/2004 | Wu et al. | 427/2.25 |

FOREIGN PATENT DOCUMENTS

| | | |
|---|---|---|
| EP | 0 850 651 | 7/1998 |
| EP | 850604 A2 * | 7/1998 |
| EP | 0 875 218 | 11/1998 |
| JP | 63-160645 | 7/1988 |
| JP | 3-14516 | 1/1991 |
| JP | 4-215768 | 8/1992 |
| JP | 8-33718 | 2/1996 |
| JP | 8-213026 | 8/1996 |
| JP | 9-85028 | 3/1997 |
| JP | 11-299901 | 2/1999 |
| WO | WO 90/01969 | 3/1990 |
| WO | WO 94/13268 | 6/1994 |
| WO | WO 95/11817 | 5/1995 |
| WO | WO 96/28115 | 9/1996 |
| WO | WO 96/32907 | 10/1996 |
| WO | WO 98/23228 | 6/1998 |
| WO | WO 99/16386 | 4/1999 |

OTHER PUBLICATIONS

Lambert et al., *Localized Arterial Wall Drug Delivery From a Polymer-Coated Removable Metallic Stent*, Circulation 90(2):1003-1011 (Aug. 1994).

De Scheerder et al., *Biocompatibility of Polymer-Coated Oversized Metallic Stents Implanted in Normal Porcine Coronary Arteries*, Atherosclerosis 114:105-114 (1995).

* cited by examiner

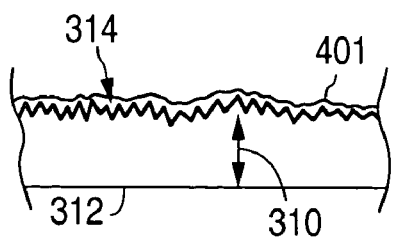
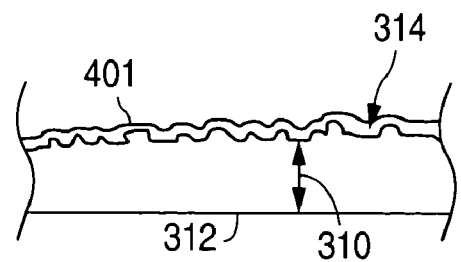
FIG. 4A          FIG. 4B
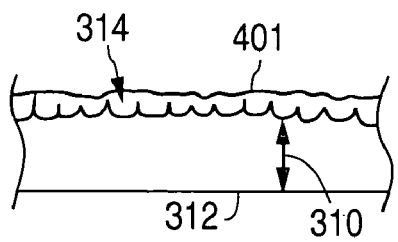
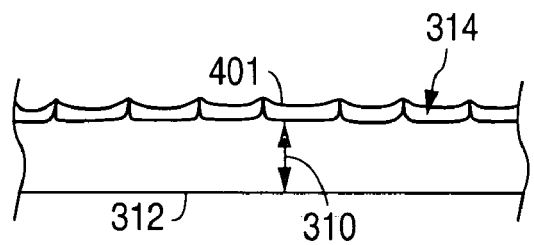
FIG. 4C          FIG. 4D
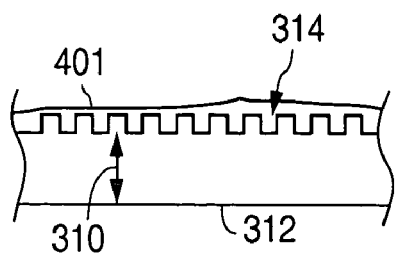
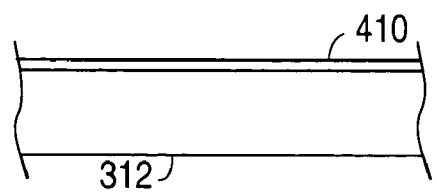
FIG. 4E          FIG. 4F
(PRIOR ART)

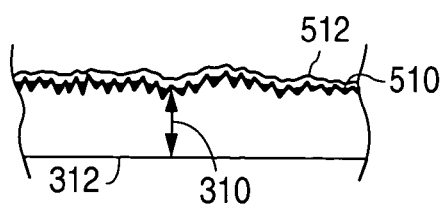
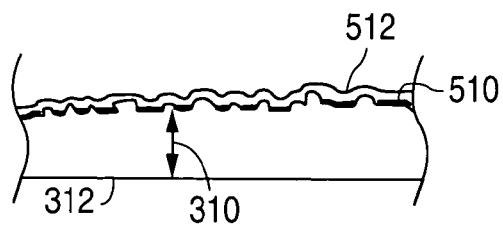
FIG. 5A  FIG. 5B
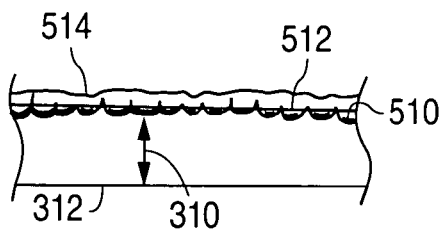
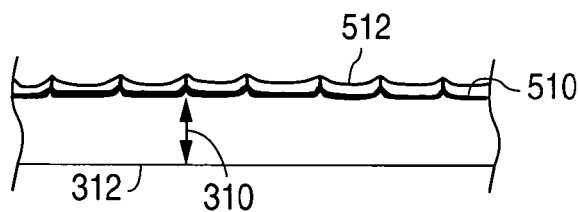
FIG. 5C  FIG. 5D
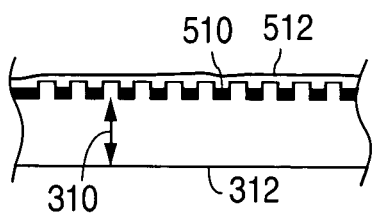
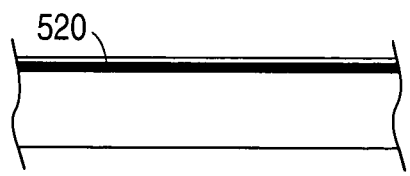
FIG. 5E  FIG. 5F
(PRIOR ART)
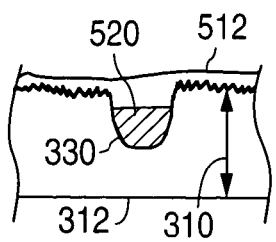
FIG. 5G

METHOD OF MAKING AN IMPLANTABLE MEDICAL DEVICE

CROSS REFERENCE

This is a divisional application of U.S. Ser. No. 09/675,092, which was filed on Sep. 28, 2000 now U.S. Pat. No. 6,805,898.

BACKGROUND OF THE INVENTION

1. Field of the Invention

This invention relates to surface features of implantable medical devices, for example stents and grafts, and to methods for forming such surface features.

2. Description of the Background

Percutaneous transluminal coronary angioplasty (PTCA) is a procedure for treating heart disease. A catheter assembly having a balloon portion is introduced into the cardiovascular system of a patient via the brachial or femoral artery. The catheter assembly is advanced through the coronary vasculature until the balloon portion is positioned across the occlusive lesion. Once in position across the lesion, the balloon is inflated to a predetermined size to radially compress against and remodel the artery wall for dilating the lumen. The balloon is then deflated to a smaller profile to allow the catheter to be withdrawn from the patient's vasculature.

A problem associated with the procedure includes formation of intimal flaps or torn arterial linings that can collapse and occlude the conduit after the balloon is deflated. Moreover, thrombosis and restenosis of the artery may develop over several months after the procedure, which may require another angioplasty procedure or a surgical by-pass operation. To reduce the partial or total occlusion of the artery by the collapse of arterial lining and to reduce the chance of the development of thrombosis and restenosis, an implantable device, an example of which includes an expandable stent, is implanted in the lumen to maintain the vascular patency. Stents are scaffoldings, usually cylindrical or tubular in shape, functioning to physically hold open, and if desired, to expand the wall of the passageway. Typically stents are compressed for insertion through small cavities via small catheters, and then expanded to a larger diameter once at the desired location. Examples in patent literature disclosing stents include U.S. Pat. No. 4,733,665 issued to Palmaz, U.S. Pat. No. 4,800,882 issued to Gianturco, and U.S. Pat. No. 4,886,062 issued to Wiktor.

A problem encountered with intravascular stents is that, once implanted into the blood stream, platelets and other blood components tend to adhere to any portion of the stent surfaces having roughness or irregularity. Adhesion and aggregation of platelets and other blood components can lead to thrombosis and restenosis. Therefore, an important aspect of manufacturing and finishing stents is ensuring that all stent surfaces are made extremely smooth, without roughness and irregularities. This is accomplished by highly polishing the entire surface of the stent material, typically by electropolishing or by using an abrasive slurry, as described in U.S. Pat. No 5,746,691 titled "Method for Polishing Surgical Stents" issued to Frantzen and U.S. Pat. No. 5,788,558 "Apparatus and method for Polishing Lumenal Prostheses" issued to Klein.

To further fight against thrombosis and restenosis, and in treating the damaged vascular tissue, therapeutic substances can be administered. For example, anticoagulants, antiplatelets and cytostatic agents are commonly used to prevent thrombosis of the coronary lumen, to inhibit development of restenosis, and to reduce post-angioplasty proliferation of the vascular tissue, respectively. To provide an efficacious concentration to the treated site, systemic administration of these drugs often produces adverse or toxic side effects for the patient. Local delivery is a highly suitable method of treatment in that smaller levels of medication, as compared to systemic dosages, are concentrated at a specific site. Local delivery therefore produces fewer side effects and achieves more effective results.

One commonly applied technique for the local delivery of therapeutic substances is through the use of medicated stents. A well-known method for medicating stents involves the use of a polymeric carrier coated onto the body of the stent, as disclosed in U.S. Pat. No. 5,464,650 issued to Berg et al., U.S. Pat. No. 5,605,696 issued to Eury et al., U.S. Pat. No. 5,865,814 issued to Tuch, and U.S. Pat. No. 5,700,286 issued to Tartaglia et al. The therapeutic substances are impregnated in, located on, or provided underneath the polymeric coating for release in situ once the stent has been implanted.

An obstacle often encountered with the use of stent coatings is poor adhesion of the polymeric coating to the surface of a stent. During stent delivery, a poorly adhering coating can be rubbed and peeled off of the stent if the coating contacts an arterial wall while the stent is being moved into position. Also, when a coated stent is expanded in situ, the distortion the stent undergoes as it expands can cause the coating to peel, crack, or tear, and disengage from the stent. Poor adhesion of the coating material can promote thrombosis and restenosis, by providing additional surfaces for platelets and other blood components to adhere. Additionally, poor adhesion and loss of the coating also leads to loss of a significant amount of the drugs to be delivered from the coating.

Another technical challenge in using stent coatings to deliver drugs is loading enough drug onto the stent, so that an effective amount of the drug or drug combination is delivered to the treatment site. The total amount of a drug that can be loaded onto a stent in a polymeric coating is limited by the amount of drug that can be mixed into the polymer (the concentration of the drug in the polymer), and the amount of polymer and drug mixture that can be coated onto the stent (the thickness of the coating on the stent for a given stent size). Therefore, a stent that carries more coating can deliver greater amounts of drugs. However, increasing the thickness of a stent coating can be difficult, particularly if the coating does not adhere well to the stent material.

When delivering drugs from a stent, it is also desirable to control the timing and rate of release of the drugs being delivered. Controlled release can be achieved by coating a stent with a number of layers. For instance, each layer can contain a different drug or be made of a polymer that releases drugs at different rates. However, additional layers tend to adhere poorly to underlying layers. The additional layers peel off either during application of the additional layer over an underlying layer, or, as described above, when the stent is delivered and expanded within the artery.

Another complication for drug delivery from a stent is that the arterial wall tissue the stent is compressed against can be tough and fibrotic, preventing medication released from the stent from penetrating the tissue in which the medication may be therapeutically beneficial.

SUMMARY

An implantable medical device capable of delivering therapeutic substances from a coating is provided, which provides a high retention of one or more layers of coating material. The implantable device also allows a greater total amount of coating to be carried by the device, allowing for greater amounts of therapeutic substances to be delivered from the device. In some embodiments the implantable device can penetrate the arterial wall to enhance delivery of therapeutic substances into the arterial wall.

In one embodiment within the present invention, the implantable medical device has a generally tubular structure with an inner surface and an outer surface. The outer surface has asperities on designated regions that have roughness factors, Ra, of greater than 40 nm. The designated regions can be the entire outer surface, a middle section of the outer surface, or ends of the outer surface. Typically, the inner surface is smooth.

In various embodiments, the outer surface, or portion thereof, can be coated with a coating containing a therapeutic substance or substances, a polymer, or a combination of therapeutic substances and polymer. The coating can be made of one or more layers and the layers can hold different therapeutic substances, polymers, or combination of therapeutic substances and polymers.

The asperities may have surface protrusions and indentations of various shapes. In some embodiments, the asperities can have sharp tips, be rounded, be square, or a combination of these shapes.

Exemplary embodiments are made by polishing the inner surface of the implantable medical device and forming asperities on the designated region of the outer surface. In some embodiments, the inner surface is polished before the asperities are formed and the inner surface is protected while the asperities are being formed.

In some embodiments, the asperities are formed by projecting grit, which can be beads or sand, at the designated region of the outer surface.

In some embodiments, the asperities are formed by depositing material onto the designated region. In one method, the material is deposited by adding particles to the designated region and bonding the particles, for instance by sintering, to the designated region. In one method, the material is deposited by sputtering. In some embodiments, the material added to the outer surface is radio-opaque.

In some embodiments, the asperities are formed by applying a chemical etchant to the designated region and rinsing the chemical etchant off of the region after a predetermined period of time. The chemical etchant can by applied by sponging or spraying the etchant onto the outer surface. In some embodiments, a patterned mask, which has openings, is applied to the outer surface and then the chemical etchant is applied, allowing the chemical etchant to etch through the openings.

In some embodiments, the asperities are formed by machining or laser cutting.

These and other features and aspects of the various embodiments of the present invention may be better understood in view of the drawings and the following detailed description.

BRIEF DESCRIPTION OF THE FIGURES

FIGS. 3F and 3G also show depots.

FIGS. 4A, 4B, 4C, 4D and 4E are cross-sectional views of portions of implantable medical devices with exemplary asperities covered with a coating.

FIG. 4F is a cross-sectional view of a portion of a conventional implantable medical device that is coated.

FIGS. 5A, 5B, 5C, 5D, and 5E are cross-sectional views of portions of implantable medical devices with exemplary asperities covered with two or three layers of coatings.

FIG. 5F is a cross-sectional view of a portion of a conventional implantable medical device that has two layers of coating.

FIG. 5G is a cross-sectional view of a portion of an implantable medical device with exemplary asperities and a depot. The depot contains a material and the material and the asperities are covered with a coating.

DETAILED DESCRIPTION

Figure 1A:
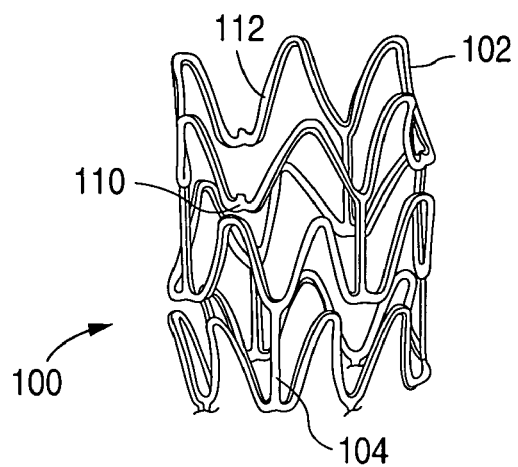
FIG. 1A is a perspective view of an example of a stent in an expanded state.
Figure 1B:
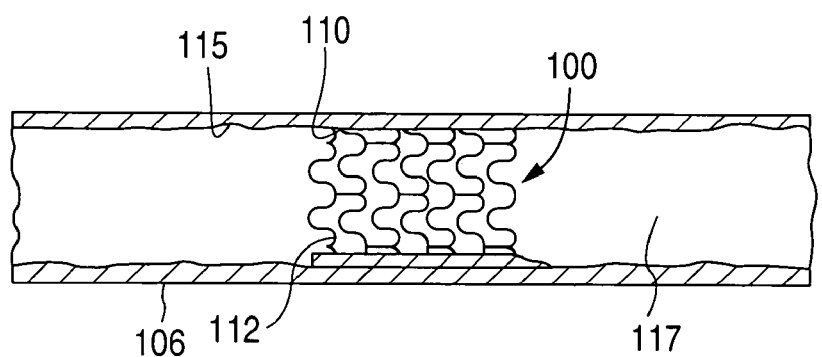
FIG. 1B is a cross-sectional side view of a stent implanted in a lumen.

The present invention includes surface treatments for implantable medical devices, such as stents and grafts, often referred to as endoprostheses. FIGS. 1A and 1B illustrate an exemplary stent 100 in accordance with one embodiment. Stents are scaffoldings, usually cylindrical or tubular in shape, which are inserted into an anatomical passageway and operate to physically hold open and, if desired, to expand or replace the wall of a passageway. Stents are capable of being compressed for insertion through small cavities via balloon-catheters, positioned in a desired location, then expanded to a larger diameter. Stents can be either balloon expandable or self-expanding.

Referring to FIG. 1A, exemplary stent 100 is a patterned tubular device that includes a plurality of radially expanding cylindrical struts 102 disposed generally coaxially and interconnected by connecting struts 104 that are disposed between and connect adjacent cylindrical struts 102. Struts 102 and 104 can be any suitable thickness T between the stent outer surface 110 and inner surface 112. Typically thickness T is in the range of approximately 50 μm (0.002 inches) to 200 μm (0.008 inches). A specific choice of thickness depends on the anatomy and size of the target lumen.

FIG. 1B illustrates stent 100 of FIG. 1A implanted in a lumen 106. The stent struts 102 and 104 define a stent body having an outer surface 110 in contact with inner surface of the lumen 115, and an inner surface 112 in contact with the fluid stream through the lumen 117. For example, when stent 100 is implanted in a blood vessel, the outer surface is in contact with the blood vessel wall, and the inner surface is in contact with the blood flowing through the vessel.

Figure 1C:
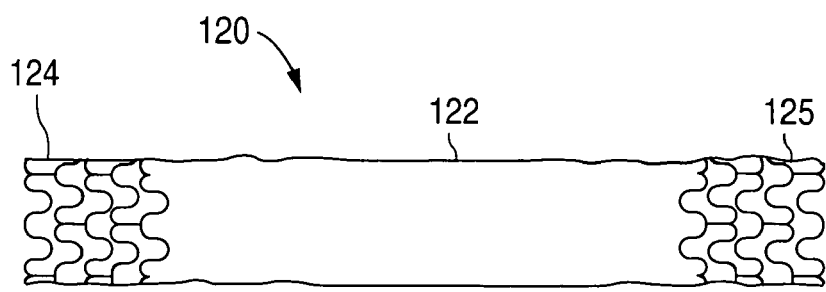
FIG. 1C is a side view of a graft.
Figure 1D:
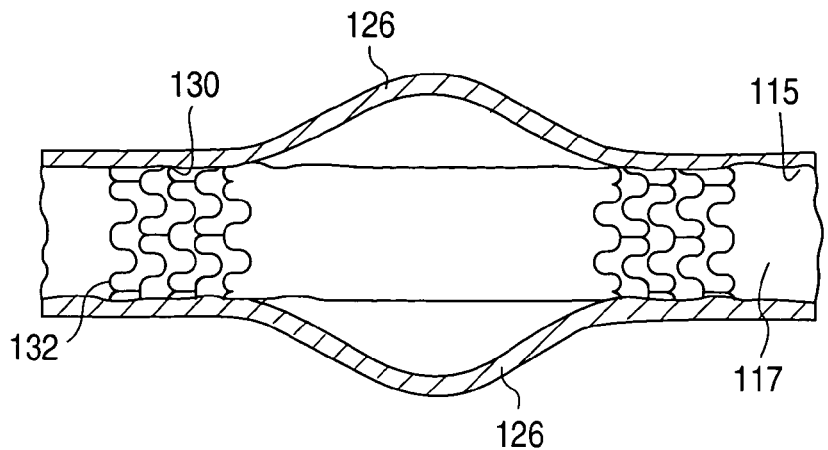
FIG. 1D is a cross-sectional side view of a graft implanted in a damaged blood vessel.

An exemplary graft 120 is illustrated in FIG. 1C. Grafts are typically placed in a blood vessel to either replace a diseased segment that has been removed, or, as illustrated in FIG. 1D, to form a bypass conduit through a damaged segment of the vessel wall, for instance, an aneurysm 126. The graft 120 has a tubular portion 122, which spans the site of the damaged tissue and through which the blood flows. The graft has sections, 124 and 125, at both ends of tube 122 that are used to secure the graft to the inside of the vessel wall 115. The graft also has an outer surface 130, portions of which are in contact with inner surface of the blood vessel wall 115, and an inner surface 132, in contact with the blood flowing through the vessel 117.

In some embodiments, the implantable device may include a single depot, or a plurality of depots, formed in an outer surface thereof. The materials may be filled, fully or partially, with a material, such as a therapeutic substance or polymer, as discussed below.

Figure 1E:
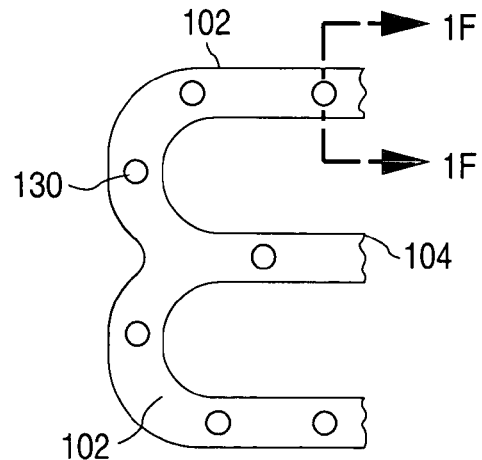
FIG. 1E illustrates a portion of the struts of the stent of FIG. 1A, which shows depots formed therein.
Figure 1F:
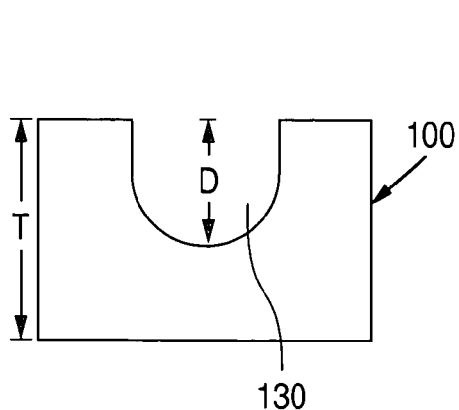
FIG. 1F is a cross-sectional side view of a stent strut, taken in the direction of the arrows and along the plane of line 1F-1F of FIG. 1E, illustrating a depot formed in strut.
Figure 1G:
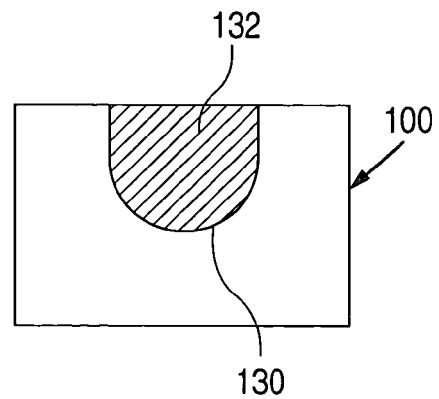
FIG. 1G illustrates the strut of FIG. 1F in which a material has been deposited into the depot.

FIGS. 1E, 1F, and 1G illustrate a portion of stent struts 102, 104 of the exemplary stent 100 having depots 130 formed in an outer surface thereof. Depots 130, which may also be referred to as a pores or a cavities, can be formed in virtually any implantable device structure. Depots 130 are formed by a manufacturer at any preselected location and have any preselected depth, size, and geometrical configuration. The location of depots 130 on the outer surface of the implantable device varies according to intended usage and application. The depth and size of depots 130 typically depend on the material and dimensions of the implantable device, the type and amount of materials deposited within depot 130, and the clinical purpose and usage of the device. Typically, depots have a depth, D, that is between 10% and 90%, e.g. 40% to 60%, of the strut thickness, T (illustrated in FIG. 1F). The depth and size of the individual depots 130 formed on a single device can vary relative to one another. Depots 130 may be formed in a variety of selected geometrical shapes including, but not limited to, generally cylindrical shapes, generally conical shapes, and elongated trenches.

In some embodiments, depots 130 contain material 132, as depicted in FIG. 1G. Depots 130 may contain a material that is the same, or different than the device covering material, as described in detail below with respect to implantable medical device covers for delivering therapeutic substances.

The conventional practice of having highly polished implantable medical device surfaces contributes to the poor adhesion problem and other problems mentioned above that are associated with coatings used on implantable devices and drug delivery from such coatings. Therefore, in accordance with the present invention, asperities are created on a designated region or regions of the surface of the implantable devices. The asperities cause the designated region to have a roughness factor, Ra, defined below, greater than about 40 nm (nanometers), which is the upper limit of roughness factors typical of polished stent surfaces. Typically, the asperities so formed cause the designated region to have a roughness factor, Ra, greater than about 100 nm.

It is often desirable for the inner surface of the implantable medical device, which contacts the blood flowing through the vessel, to be smooth, in order to prevent aggregation of platelets from the blood on the stent. The outer surface of the implantable devices, which contacts the arterial wall, need not be smooth. Therefore, the designated region or regions having the asperities are typically on the outer surface of the implantable device.

Figure 2:
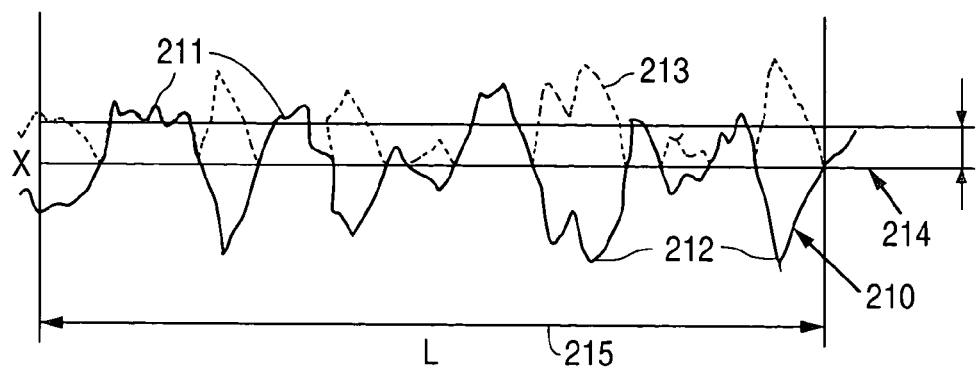
FIG. 2 graphically depicts elements used in determining the roughness factor, Ra, of a surface.

A roughness factor, Ra, is used to quantify the surface roughness. In FIG. 2, a surface having asperities is outlined in two-dimensions by the profile 210. Profile 210 outlines the irregular protrusions 211 and indentations 212 of a surface having asperities. The roughness factor, Ra, is defined herein as the arithmetic mean of the absolute values of the profile departures 213 from a centerline 214 through profile 210, within an evaluation length 215. For a three-dimensional surface, centerline 214 becomes a mean plane and Ra is defined as the arithmetic mean of the absolute values of the surface departures from the mean plane within an evaluation area. The digital approximation for the three-dimensional Ra over an evaluation area is given in Equation 1:

$$R_a = \frac{1}{MN} \sum_{j=1}^{M} \sum_{i=1}^{N} |Z_{ji}| \qquad \text{Equation 1}$$

M and N are the number of data points in the X and Y directions, respectively, of the evaluation area, and Z is the surface height of each point relative to the mean plane.

The roughness factor, Ra, of asperities on an implantable medical device within the present invention may be measured, for example, by using a commercially available Veeco Metrology Group (Tucson, Ariz.) WYKO NT-2000 system, which is a non-contact optical profiler. VSI (vertical scanning interferometer) mode is used. For cylindrical implantable medical devices, such as stents, cylinder and tilt terms are removed so the stent surface appears flat. A low pass filter is used which removes the effects of high spatial frequency roughness, smoothing over features that are smaller than a nine pixel window. A 50× objective and 2.0× FOV converter sense are used to produce an effective magnification of 100×. This objective and converter combination profiles a 0.58 μm×0.44 μm evaluation area, at a spatial sampling interval of 159.13 nm. For statistical purposes, samples are measures at five separate locations. Equation 1 is used to calculate a value of Ra.

In general, outer surface asperities in accordance with the present invention can have a variety of shapes, some examples of which are illustrated in FIGS. 3A-3E. FIGS. 3A-3E illustrate cross-sectional views of portions of implantable devices (for example, portions of stent struts, 102 or 104) with average thicknesses 310 and inner surfaces 312. Outer surface asperities 314 can be random and irregular, as exemplified in FIGS. 3A and 3B. The asperities 314 can also be more regular and well-defined, as exemplified in FIGS. 3C, 3D, and 3E. The asperities of the embodiments can be formed by protrusions and indentations in the surface that can have a variety of shapes and sizes, for example, the rounded shape 318 of FIG. 3B, the pointed shape 319 of FIG. 3D, or the rectangular shape 315 of FIG. 3E. In the exemplary surface of FIG. 3E, the protrusion and indentations cause the surface to have ridges 316 and channels 317. The protrusions and indentations can also have different densities on the surface, as illustrated by the difference between FIGS. 3C and 3D.

Figure 3A:
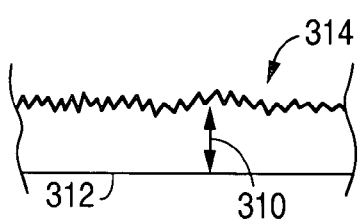
FIGS. 3A, 3B, 3C, 3D, 3E, 3F, and 3G are cross-sectional views of portions of implantable medical devices with exemplary asperities.
Figure 3B:
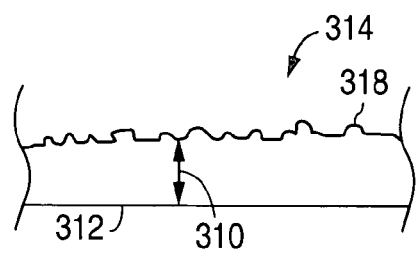
Figure 3C:
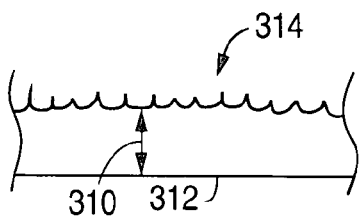
Figure 3D:
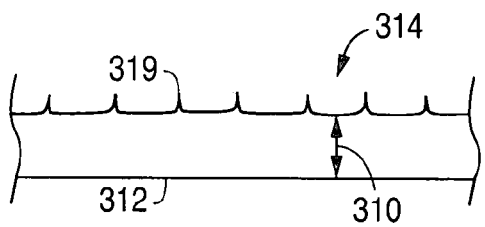
Figure 3E:
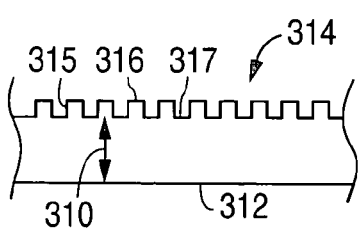
Figure 3F:
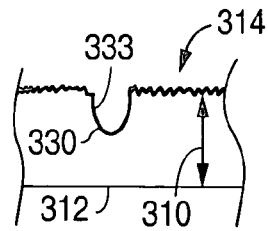
Figure 3G:
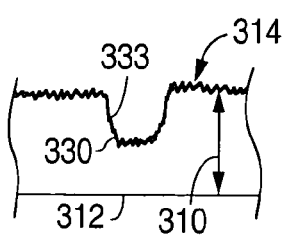

As illustrated by the exemplary surfaces in FIGS. 3F and 3G, the asperities 314 may be formed on an implantable medical device that has depots 330. Note that depots 330 have a greater depth than the asperities 314. The depot surface 333 may be smooth, as illustrated in FIG. 3F, or depot surface 333 may contain asperities 314, as illustrated in FIG. 3G.

FIGS. 4A-4E illustrate coatings 401 covering the example surfaces illustrated in FIGS. 3A-3E. Coating 401 may be, for example, a polymeric coating that contains a therapeutic substance, as described in detail below. As compared to the coated smooth surface 410 (FIG. 4F) of a conventional coated implantable medical device, the asperities of the present invention provide a mechanical hold for the coating and help to prevent the coating from slipping or peeling off of the implantable device. The asperities also provide greater surface area on the implantable device, increasing the amount of coating that can be put onto the surface. The greater amount of coating allows the implantable device to carry more therapeutic substance, so more medicine can be delivered from the implantable device in situ. The coating may fully cover the asperities or the peaks of the asperities may extend through the coating.

The asperities can also allow two or more layers of a coating to adhere to an implantable device, as illustrated in FIGS. 5A-5E. A first layer 510 is coated onto the surface and then covered with a second layer, 512, or even third layer 514 (FIG. 5C). The first coating 510 partially fills the depth of the areas between the asperities, but the peaks of some or all of the asperities extend above the coating 510. Because of the asperities, the second (and third) layer can adhere to both the first layer and protruding implantable device material, as can be seen by comparison to a conventional smooth stent with two layers, FIG. 5F.

The multiple coating layers of FIGS. 5A-5E can be used to achieve different therapeutic substance release profiles. For example, if it is desired to release two therapeutic substances sequentially, one followed by the other, two layers as illustrated in FIGS. 5A, 5B, 5D, and 5E can be used. A therapeutic substance in the outer layer 12 will be released first, as the outer layer dissolves, and a therapeutic substance in the underlying layer 10 will be released after the outer layer 12 has wholly or partially dissolved. This release profile is sometimes referred to as a "late burst," especially if the second therapeutic substance to be released (that in the underlying layer 10) is in a highly soluble form, for instance, pure crystalline form. It should also be noted that, in accordance with the present invention, the underlying layer can be made of a material that does not adhere well to the surface, because the outer layer can be used to hold the underlying layer onto the implantable device. As shown in FIGS. 5A-5E, the outer layer 512 can adhere to portions of the surface not covered by the underlying layer, and thus act as a seal for an underlying layer.

If the implantable device contains depots 330 (as illustrated in FIG. 5G), the therapeutic substance release profile can be manipulated even further. The coating layer 512 on the outer surface of the implantable device and over depots 330 will need to partially or wholly dissolve before the material 520 deposited in depots 330 is exposed and can begin to dissolve and release the therapeutic substance. Thus, release of the material deposited in the depots 330 can be delayed by application of the coating layer 512.

If the asperities are sharp, having, for instance, sharp protrusions as in 319, FIG. 3D, or sharp edges, they can also penetrate the tissue of the lumen once the implantable device is expanded. The penetration may enhance the ability of therapeutic substances released from the coating to reach target cells. Sharp asperities may also help to hold the implantable device in place in the lumen, which may be particularly useful with grafts, which need to be affixed to the lumen at the distal and proximal end of the damaged tissue. In these cases, the asperities can be formed on the distal and proximal ends of the graft.

In the discussion that follows, methods are described for forming asperities on the outer surface of a stent, as an example of an implantable medical device. It is to be understood that, in accordance with the invention, these methods can be applied to any implantable medical device, including grafts and other implantable devices.

In one method for manufacturing a stent, a thin-walled, small diameter, cylindrical tube is cut to produce the desired stent pattern. Cutting is typically accomplished through laser cutting, as described in U.S. Pat. No. 5,759,192 "Method and Apparatus for Direct Laser Cutting of Metal Stents" to Saunders, or chemical etching, as described in U.S. Pat. No. 6,056,776 "Expandable Stents and Method of Making Same" to Lau et al. Other methods of cutting stent lattice patterns can be used. Instead of cutting the pattern into a tube, the stent lattice pattern can be cut into a flat sheet of material, which is then rolled and joined in a cylindrical configuration.

The tube or flat sheet used to form the stent may be made of any suitable biocompatible material such as a metallic material or an alloy, examples of which include, but not limited to, stainless steel, "MP35N," "MP20N," elastinite (Nitinol), tantalum, nickel-titanium alloy, platinum-iridium alloy, gold, magnesium, or combinations thereof. "MP35N" and "MP20N" are trade names for alloys of cobalt, nickel, chromium and molybdenum available from standard Press Steel Co., Jenkintown, Pa. "MP35N" consists of 35% cobalt, 35% nickel, 20% chromium, and 10% molybdenum. "MP20N" consists of 50% cobalt, 20% nickel, 20% chromium, and 10% molybdenum. The stent also may be made from bioabsorbable or biostable polymers.

Often, cutting the stent lattice pattern, especially by laser, leaves scrap that must be removed, in a process known as descaling, to reveal the lattice pattern of the stent. Descaling is typically accomplished by ultrasonically cleaning the stent in heated acid, as described in U.S. Pat. No. 5,759,192. The stent is also polished so the stent surfaces are made as smooth as possible. In conventional processes, a cleaning or rinsing step, usually with an alcohol solution, follows the polishing step to remove any of the polishing solution that may be left on the stent.

Another method that is used to manufacture stents is to mold the stent into the desired shape. This method is especially useful if the stent is made from a polymeric material. Polishing is sometimes done after molding to ensure smooth stent surfaces.

Depots 130, 330 may be formed as a laser trench on the implantable device by exposing the surface to an energy discharge from a laser, such as an excimer laser. Alternative methods of forming such depots 130, 330 include, but are not limited to, physical and chemical etching techniques. Techniques of laser fabrication or etching to form depots are well-known to one of ordinary skill in the art. Depots 130, 330 may be added before or after the asperities are formed In general, the asperities may be added to the outer surface of the stent at any point in the stent manufacturing process, provided that subsequent processing does not remove the asperities desired in the completed stent.

For example, in one embodiment, the asperities on the stent outer surface are created after the stent has been polished. In this case the smooth inner surface is protected during creation of the asperities to preserve the smoothness of the inner surface. This may be done, for example, by inserting a mandrel or a hypo tube inside the stent or inserting and inflating a balloon inside the stent. The inner surface can also be masked with a temporary protective coating, which is removed after the asperities have been added to the outer surface of the stent. For example, a poly vinyl alcohol (PVA) solution (80% by weight dissolved in hot water at 100° C.) can be applied to the inner surface with a syringe and allowed to air dry, and can be removed by soaking in water. In another embodiment, the asperities are created before the stent pattern is cut. In these cases, the asperities need to be preserved when the stent is cut, descaled, and polished, and therefore this embodiment works well with asperities that are not likely to be destroyed in subsequent processing. If subsequent processing might destroy the asperities, a temporary protective coating can be applied to the outer surface of the stent to preserve the asperities.

If the stent contains depots, the asperities can be formed either before or after formation of the depots, depending on the methods used to form the depots and the asperities. In some methods, if the asperities are formed after the depots, the surface of the depots may also be roughened.

METHODS OF TREATING THE SURFACE

A. Mechanical Methods for Creating Asperities

Figure 6A:
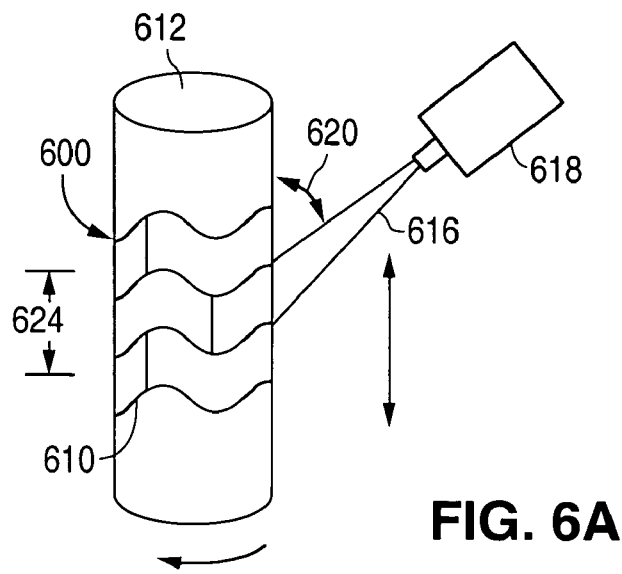
FIG. 6A is a schematic representation of the method of using a pressurized grit source to create asperities on the outer surface of a stent while protecting the inner surface of the stent.

A variety of methods can be used to create the asperities on the outer surface of the stent. FIG. 6A illustrates one embodiment, in which a pressurized stream of grit material is directed upon the outer surface 610 of stent 600 to create asperities on the outer surface of the stent. Examples of such processes include bead blasting and sand blasting. Bead blasting refers to the use of pressurized gas to project beads of relatively uniform diameter at an object at a high velocity. The bead may be made of a variety of materials, such as latex, aluminum oxide, or silicon oxide. In sand blasting, the grit projected does not have as uniform a diameter as in bead blasting. Both bead blasting and sand blasting are techniques that are well known in the art.

In FIG. 6A, the stent 600 which has been polished, is mounted onto a mandrel 612 to protect the stent's inner surface during blasting. The stent is then rotated while the grit 616, e.g., beads, is projected at the stent outer surface from the pressurized grit source 618. The grit is projected at the stent at an approximately 30° angle 620 to the vertical axis of the stent, and is passed up and down over the outer surface 610 of the stent until the desired pattern, type, and number of asperities have been created. The visual appearance of the surface can be used to indicate that it is roughened appropriately. The outer surface of the stent is smooth, shiny, and reflective before the process, but becomes dull, non-reflective, and of a darker color shade after the roughening process. Subsequently, the stent is removed from the mandrel and cleaned, for example by immersion and sonication in an isopropyl alcohol bath for approximately 20 minutes.

The roughness factor achieved using a pressurized grit source can be controlled by the size of the grit, e.g., the diameter of the beads, the pressure used, the distance between the grit source and the stent surface, and the length of time the grit is blasted at the surface. By way of example and not limitation, the grit can be beads having a diameter of between 10 µm and 50 µm. Pressures of 30 PSI (pounds per square inch) to 60 PSI can be used to project the beads from a distance of approximately 3-10 cm from the stent. The grit source is passed very quickly, in approximately 1-3 seconds, down and up over the stent outer surface. The stent is then rotated 120° and the process repeated twice so the entire stent is roughened.

Average roughness values achieved are typically in a range of 100 nm to 300 nm, and usefully in a range of 130 nm to 210 nm.

Figure 6B:
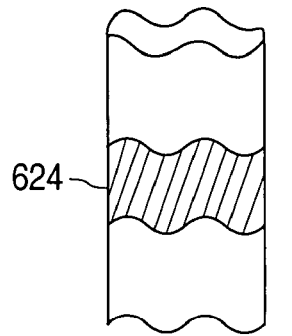
FIG. 6B is a schematic representation of a stent having asperities on a middle portion.
Figure 6C:
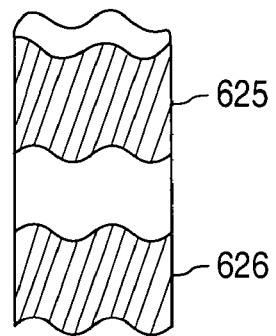
FIG. 6C is a schematic representation of a stent having asperities adjacent to the ends of the stent.

Note also, that the entire outer surface need not be roughened. For example, the grit may be projected at only a middle region 624 (FIGS. 6A and 6B) of the stent, so that the asperities are formed only in a middle region of the stent's outer surface, and not adjacent to the opposing ends of the stent, FIG. 6B. Or, as illustrated in FIG. 6C, the grit may be projected only at the ends of the stent, to create asperities at one or both ends, 625 and 626.

If the stent contains depots, the depots may be in regions where there are asperities, may be in regions where there are not asperities, or both.

Figure 7A:
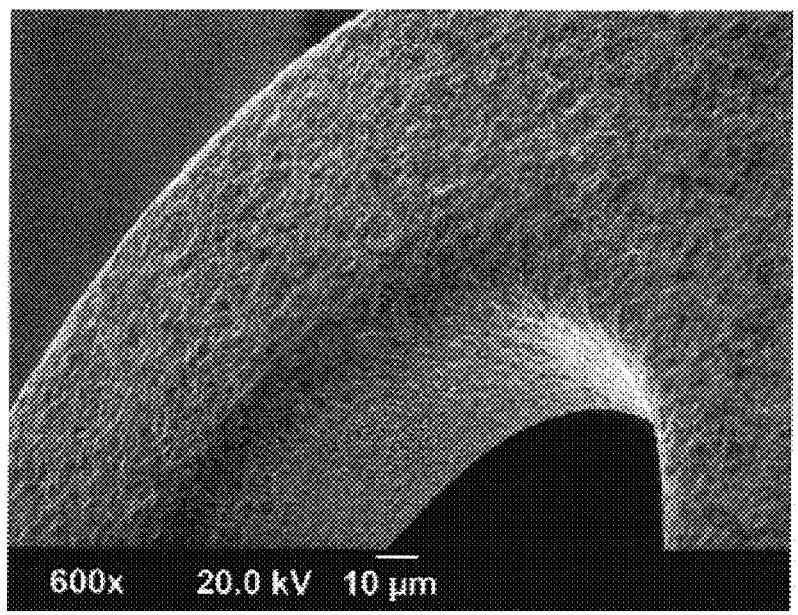
FIGS. 7A and 7B are scanning electron micrograph photographs of portions of stent surfaces on which asperities have been created by bead blasting.
Figure 7B:
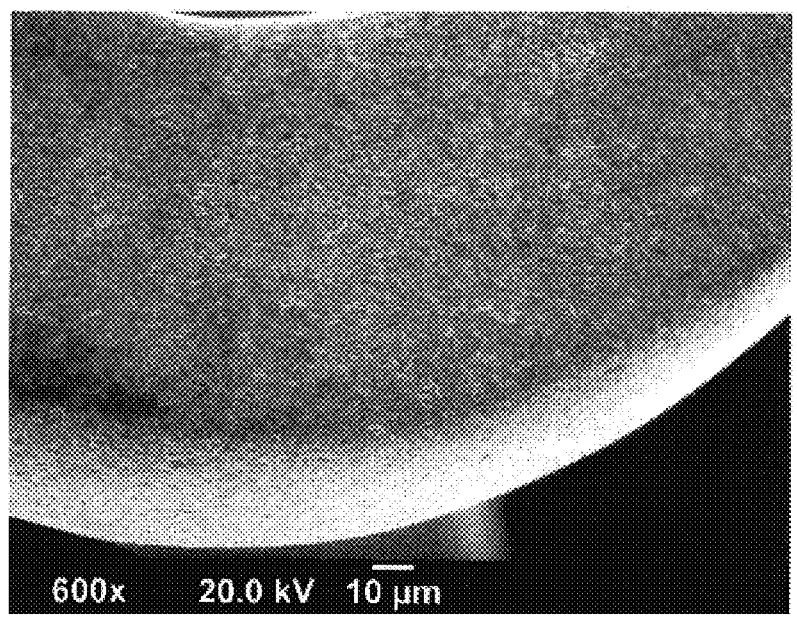

FIGS. 7A and 7B are scanning electron micro graph photographs of portions of stent struts (e.g., 102 of FIG. 1A) having asperities created by bead blasting (as described above). The stent material in the examples shown in the photographs is 316L stainless steel. The photographs show the outer surface of the struts, which have been roughened. The asperities in FIG. 7A were created using a pressure of 60 PSI, and the asperities in FIG. 7B were created using a pressure of 30 PSI. The photographs also show the surfaces of the sides of the struts, which were also roughened during the bead blasting process. In other embodiments, the sides of the struts may be left smooth or asperities can be added to only a portion thereof.

In another embodiment, the asperities may be formed by grinding the tubular stent between two sanding plates or using sandpaper to scratch the outer surface. In this method, the roughness factor achieved depends on the grain size of the surface of the sanding plates. This method may be particularly useful with polymer stents or stents made from relatively soft materials. Typically, this method is used to create asperities after the stent pattern has been cut into the hypotube (or cut into a flat piece of material and the material rolled into a tube), and after the stent has been descaled, if descaling is necessary, and polished.

B. Creating Asperities by Removal of Stent Material

In another embodiment, chemical etching is used to create asperities on the outer surface of a stent. Chemical etching methods are known to those of ordinary skill in the art. The chemical etchant solution typically includes an acid that degrades and dissolves the material from which the stent is made. The chemical etchant is applied to the outer surface, and then rinsed off of the surface after a predetermined period of time. The length of time the etchant is left on the surface depends on the etch rate and the depth of etch desired.

The roughness factor produced by the chemical etchant depends on the method of application of the etchant. In one embodiment, the chemical etchant is applied to the stent outer surface with a fine sponge or by spraying a mist of the chemical etchant onto the stent. A temporary protective coating, e.g., poly vinyl alcohol dissolved in water, is applied to the inner surface of the stent to protect the inner surface from the etchant to keep the inner surface smooth. The chemical etchant is rinsed off of the stent, leaving a rough outer surface. The roughness factor will depend on the stent material and the chemical etchant used, the amount and length of time the etchant was applied, and how the etchant was applied.

In one embodiment, the stent is made of a composite material where one of the components of the composite material can be easily dissolved by the chemical etchant. For example, a metal alloy, such as stainless steel can be used to form the stent and nitric acid can be applied to the outer surface to create the asperities. A hydrochloric acid solution, 37% by volume in water, can also be used to create the asperities.

In another embodiment, a patterned mask that has openings is applied to the stent outer surface before the chemical etchant is applied. The etchant is then applied in a uniform manner and allowed to etch the stent material through the openings of the mask. The use of patterned masks with chemical etchants is known to those of ordinary skill in the art. Because it is usually easier to mask and etch a flat piece of material than a hypo-tube, the mask is typically applied to a flat piece of the stent material and the resulting outer surface pattern etched into the surface. Then, the flat piece of stent material is cut, rolled and joined into a stent. The flat piece of stent material may be polished before the mask and etch process, so that the asperities created by the mask and etch are not degraded in a subsequent polishing process. Additionally, a cutting process that does not leave scrap between the stent struts can be used to eliminate the descaling step, which may also damage the asperities. For example, the stent pattern can be cut using another chemical etching step where the second mask, which protects the asperities, is in the pattern of the stent and the etchant is allowed to dissolve all material not masked.

In this embodiment, the patterned mask can be used to make asperities that are composed of more regular and well-defined shapes. The shapes can be chosen depending on the eventual application of the stent. In one example, a patterned masking followed by etching is used to create asperities composed of relatively sharp tips (319 of FIG. 3D), or ridges and channels (316 and 317, respectively, of FIG. 3E). The sharp tips 319 can have a height between 0.1 µm and 10 µm. The sharp tips can be of any density on the surface, although a higher density produces more surface area, provides better mechanical hold of the coating, and has more tips to penetrate the tissue. The asperities made by this method typically have a roughness factor between 50 nm and 5 µm.

If, when creating the asperities by chemical etching, a significant amount of stent material will be removed, for instance to reduce the average thickness T of the stent strut by more than 10%, a thicker material can be used to form the stent. Therefore, the finished stent has the desired strut thickness T after etching so that the structural integrity of the stent is not compromised by creating the asperities.

In other embodiments, asperities are formed by machining or laser cutting the outer surface. These methods can also be used to make asperities composed of more regular and well-defined shapes. For example, a laser discharge machine tool can be programmed to cut a desired pattern into the outer surface of a stent. Because machining and laser cutting will typically remove material from the stent, a thicker material can be used to form the stent, resulting in a completed stent having the desired average strut thickness.

C. Creating Asperities by Adding Material

In another embodiment, additional material is deposited onto the outer surface of the stent to create the asperities. In one method, the additional material, which is typically a metal, is first made into a powder. The powder particles are then bonded to the outer surface to form the asperities. The powder can be made, for example, by grinding the metal to form particles of a predetermined size. The particles are then put onto the outer surface of the stent, for example, by rolling the stent in the powdered metal or spaying the powdered metal onto the stent. The stent can be electrostatically charged to a charge, typically negative, that is opposite that of the powdered metal, to improve the adhesion of the powder to the stent.

The stent coated with the particles is then heated to weld the particles to the stent by methods, for example sintering in a furnace or with a flame, known to those of skill in the art. Typically, the stent material, particle material, and sintering temperature are chosen so that melting temperatures of the materials allow the particles to be welded to the stent without distortion of the stent by the heat treatment. For example, the stent material may be 316L stainless steel and the particles may be gold, aluminum, or copper. The sintering temperature would have to be below the melting temperature of 316L stainless steel, 1388° C.

In this method, the inner surface can be protected by inserting a mandrel or applying a temporary coating to the inner surface that prevents the particles from contacting and staying on the inner surface when they are applied to the stent. The coating, typically a polymeric material, will burn off of the stent in the subsequent heat treatment. The temporary coating can also be used on the outer surface of the stent if it is desired to create asperities on only designated regions of the outer surface. For example, if it is desired to have the asperities adjacent to the ends of the stent (as illustrated in FIG. 6B), the temporary coating can be applied to the middle portion of the stent before the particles are applied to the stent.

The roughness factor, Ra, achieved using this method depends on the size of the particles in the powder and is in the range of 50 nm to 5 µm.

Figure 8:
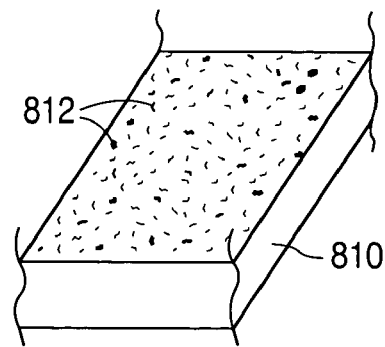
FIG. 8 is a perspective view of a portion of a stent with asperities on the top surface deposited by sputtering material onto the top surface.

The additional material may also be added via physical deposition processes, for example, sputtering, which is known to those of ordinary skill in the art. In sputtering, an energy beam, for instance an ion beam, is directed at a target formed of the material which is to be deposited on the substrate. The energy beam dislodges atoms of the target material. The target material atoms are transported to the substrate, which in this instance is the stent on which asperities are being formed. Once at the substrate, the atoms form "islands", or small nodules of the deposition material on the substrate. FIG. 8 illustrates the "islands" 812 formed on an illustrative portion of the substrate 810, corresponding to the stent outer surface (310 of FIG. 3).

Conventionally, sputtering is used to form a thin film of the deposition material over the substrate, and sputtering conditions are used such that the "islands" grow, spread, and condense on the substrate to form a thin film. To form the asperities, however, the sputtering process conditions are set so that instead of creating a uniform film over the substrate, the "islands" do not grow, spread, and condense, leaving a rough surface. Process conditions in which a lower pressure and shorter deposition time than is typically used for thin film deposition are used to form the asperities.

Typically, a cut stent is inserted into the sputtering chamber, with the inner surface protected, and rotated while material is deposited on the outer surface. Alternatively, material can be deposited onto the hypo-tube before the stent pattern is cut into it, or a flat piece of stent material before it is cut and rolled into a stent. If the subsequent processing of the stent will destroy the added asperities, a temporary protective coating can be applied to protect them.

The sputtering, however, may only loosely deposit the material onto the outer surface of the stent. In such cases, to further enhance attachment of the deposited material to the substrate, a heat treatment, for instance sintering can be performed. As discussed above, the temperature ranges for heating will depend on the deposition material and the stent material. The roughness factor achieved in this embodiment will have a lower value of approximately 50 nm and an upper value of approximately 200 nm.

Typically, material is added to the outer surface after the stent is polished, although it can be done at any point in the process provided the subsequent processes do not remove the asperities. This will again depend on the material that is used to manufacture the stent and the material deposited on the stent.

In one embodiment, radiopaque materials are deposited on the stent, to not only create asperities on the stent, but to allow visualization of the stent after implantation. For example, the radio-opaque material can be applied adjacent to the ends of the stent.

COATINGS FOR DELIVERING THERAPEUTIC SUBSTANCES

Methods of coating an implantable medical device with a therapeutic substance or substance, or with a polymer containing one or more therapeutic substances are known to one of ordinary skill in the art. One or more therapeutic substances can be added to an implantable medical device by dissolving or mixing the therapeutic substances in a solvent and applying the therapeutic substance and solvent mixture to the implantable medical device. To cover the implantable device with a polymer containing the therapeutic substance or substance combination, a solution of the polymeric material and one or more therapeutic substances are mixed, often with a solvent, and the polymer mixture is applied to the implantable device. An implantable device can also be coated with a polymer which does not contain a therapeutic substance, for example, to form a sealant layer over an underlying layer, which does contain a therapeutic substance.

Methods of applying the therapeutic substance, polymer, or therapeutic substance and polymer mixture to the implantable medical device are known to those of skill in the art. Methods include, but are not limited to, immersion, spray-coating, sputtering, and gas-phase polymerization. Immersion, or dip-coating, entails submerging the entire implantable device, or an entire section of the implantable device, in the mixture. The implantable device is then dried, for instance in a vacuum or oven, to evaporate the solvent, leaving the therapeutic substance or therapeutic substance and polymer coating on the implantable device. Similarly, spray-coating requires enveloping the entire device, or an entire section of the device, in a large cloud of the mixture, and then allowing the solvent to evaporate, to leave the coating. Sputtering typically involves placing a polymeric coating material target in an environment, and applying energy to the target such that polymeric material is emitted from the target. The polymer emitted deposits onto the device, forming a coating. Similarly, gas phase polymerization typically entails applying energy to a monomer in the gas phase within a system set up such that the polymer formed is attracted to a stent, thereby creating a coating around the stent.

If the implantable device contains depots (130 of FIGS. 1E, 1F, and 1G), it is desirable to first deposit material (132 of FIG. 1G) into the depots before coating the outer surface of the device. Materials deposited into the depots are similar to those used to cover the device, and include, for example polymers, therapeutic substances, or a combination thereof.

Materials 132 may be deposited into depots using any suitable method. In an exemplary method of depositing material 132 into depots 130, material 132 is added to a first solvent. Material 132 is dispersed throughout the first solvent so that material 132 is in a true solution, saturated or supersaturated with the first solvent or suspended in fine particles in the first solvent. The first solvent can be virtually any solvent that is compatible with material 132. A high capillary permeation and a viscosity not greater than about ten centipoise allows the first solvent to penetrate into depots 130 more quickly, eliminating a requirement to apply the first solvent to the implantable device for a prolonged period of time. Examples of suitable first solvents include, but are not limited to, acetone, ethanol, methanol, isopropanol, tetrahydrofuran, and ethyl acetate. The first solvent containing material 132 is applied to the implantable device, for example by immersing or spraying the solvent using procedures that are well-known to one having ordinary skill in the art. The first solvent containing material 132 is applied for a predetermined period of time, the specific time depending on the capillary permeation and viscosity of the first solvent, the volume of depots 130, and the amount of material 132 to be deposited.

After applying the first solvent containing material 132 for a selected duration, the first solvent is removed from the implantable device using conventional techniques, such as evaporation in ambient pressure, room temperature and anhydrous atmosphere and/or by exposure to mild heat (e.g., 60° C.) under vacuum condition. The implantable device typically has a clustered or gross formation of material 132 gathered on the body surface. The cluster is generally removed by immersing the device in a non-solvent and agitating the implantable device via mechanical perturbation techniques, such as vortexing or vigorous shaking. The non-solvent can have a low capillary permeation or a contact angle greater than about 90° and a viscosity not less than about 0.5 centipoise so that the second fluid is not capable of significantly penetrating into depots 130 during the process of agitation. Examples of a suitable non-solvent include, but are not limited to, saturated hydrocarbons or alkanes, such as hexane, heptane, and octane.

The implantable device is rinsed in a second solvent to facilitate dissolution of material 132. The second solvent generally has a low capillary permeation and a viscosity of not less than about 1.0 centipoise and is therefore incapable of significantly penetrating into depots 130 during the rinsing stage. The rinsing is conducted rapidly for example in a range from 1 second to about 15 seconds, the exact duration depending on the solubility of material 132 in the second solvent. Extended duration of exposure of the implantable device to the second solvent may lead to the penetration of the second solvent into depots 130. The rinsing step is repeated, if desired, until all traces of material 132 are removed from the surface of the implantable device. The second solvent removes excess material 132 from the surface of the implantable device body. Useful examples of second solvents include, but are not limited to, dimethylsulfoxide (DMSO), water, DMSO in an aqueous solution, glyme, and glycerol. The second solvent is removed from the implantable device body using conventional techniques. The first and second solvents as well as the non-solvent are selected to not adversely affect the characteristics and composition of material 132. Although one method of depositing material 132 into depots 130 has been described here, depots 130 may be filled using any suitable method.

Once the depots have been filled, a coating can be applied to the outer surface of the implantable device, as described above.

The polymer used for coating the implantable device and filling depots is typically either bioabsorbable or biostable. A bioabsorbable polymer bio-degrades or breaks down in the body and is not present sufficiently long after implantation to cause an adverse local response. Bioabsorbable polymers are gradually absorbed or eliminated by the body by hydrolysis, metabolic process, bulk, or surface erosion. Examples of bioabsorbable, biodegradable materials include but are not limited to polycaprolactone (PCL), poly-D,L-lactic acid (DL-PLA), poly-L-lactic acid (L-PLA), poly (lactide-co-glycolide), poly(hydroxybutyrate), poly(hydroxybutyrate-co-valerate), polydioxanone, polyorthoester, polyanhydride, poly(glycolic acid), poly(glycolic acid-cotrimethylene carbonate), polyphosphoester, polyphosphoester urethane, poly(amino acids), cyanoacrylates, poly(trimethylene carbonate), poly(iminocarbonate), copoly(etheresters), polyalkylene oxalates, polyphosphazenes, polyiminocarbonates, and aliphatic polycarbonates. Biomolecules such as heparmn, fibrin, fibrinogen, cellulose, starch and collagen are typically also suitable. Examples of biostable polymers include Parylene®, Parylast®, polyurethane (for example, segmented polyurethanes such as Biospan®), polyethylene, polyethylene teterephthalate, ethylene vinyl acetate, silicone and polyethylene oxide.

Therapeutic substances can include, but are not limited to, antineoplastic, antimitotic, antiinflammatory, antiplatelet, anticoagulant, antifibrin, antithrombin, antiproliferative, antibiotic, antioxidant, and antiallergic substances as well as combinations thereof. Examples of such antineoplastics and/or antimitotics include paclitaxel (e.g., TAXOL® by Bristol-Myers Squibb Co., Stamford, Conn.), docetaxel (e.g., Taxotere® from Aventis S.A., Frankfurt, Germany), methotrexate, azathioprine, vincristine, vinbiastine, fluorouracil, doxorubicin hydrochloride (e.g., Adriamycin® from Pharmacia & Upjohn, Peapack N.J.), and mitomycin (e.g., Mutamycin® from Bristol-Myers Squibb Co., Stamford, Conn.). Examples of such antiplatelets, anticoagulants, antifibrin, and antithrombins include sodium heparin, low molecular weight heparins, heparinoids, hirudin, argatroban, forskolin, vapiprost, prostacyclin and prostacyclin analogues, dextran, D-phe-pro-arg-chloromethylketone (synthetic antithrombin), dipyridamole, glycoprotein IIb/IIIa platelet membrane receptor antagonist antibody, recombinant hirudin, and thrombin inhibitors such as Angiomax™ (Biogen, Inc., Cambridge, Mass.). Examples of such cytostatic or antiproliferative agents include angiopeptin, angiotensin converting enzyme inhibitors such as captopril (e.g., Capoten® and Capozide® from Bristol-Myers Squibb Co., Stamford, Conn.), cilazapril or lisinopril (e.g., Priivil® and Prinzide® from Merck & Co., Inc., Whitehouse Station, N.J.), calcium channel blockers (such as nifedipine), colchicine, fibroblast growth factor (FGF) antagonists, fish oil (omega 3-fatty acid), histamine antagonists, lovastatin (an inhibitor of HMG-CoA reductase, a cholesterol lowering drug, brand name Mevacor® from Merck & Co., Inc., Whitehouse Station, N.J.), monoclonal antibodies (such as those specific for Platelet-Derived Growth Factor (PDGF) receptors), nitroprusside, phosphodiesterase inhibitors, prostaglandin inhibitors, suramin, serotonin blockers, steroids, thioprotease inhibitors, triazolopyrimidine (a PDGF antagonist), and nitric oxide. An example of an antiallergic agent is permirolast potassium. Other therapeutic substances or agents that may be used include alpha-interferon, genetically engineered epithelial cells, and dexamethasone. In other examples the therapeutic substance is a radioactive isotope for implantable device usage in radiotherapeutic procedures. Examples of radioactive isotopes include, but are not limited to, phosphoric acid ($H_3P^{32}O_4$), palladium ($Pd^{103}$), cesium ($Cs^{131}$), and iodine ($I^{125}$). While preventative and treatment properties of the foregoing therapeutic substances or agents are well-known to those of ordinary skill in the art, the substances or agents are provided by way of example and are not meant to be limiting. Other therapeutic substances are equally applicable for use with the disclosed methods and compositions.

The following example illustrates a method for creating asperities on an outer surface of a stent, and then coating the stent. The results are compared to the result obtained for a stent coated in the same manner but without a roughened outer surface. The example is given by way of illustration and not limitation.

EXAMPLE

Stents #1-5 were fabricated by cutting, descaling, and polishing a 316L stainless steel hypo-tube as described in U.S. Pat. No. 5,759,192. The inner surface of stents #1-#4 were protected by inserting a mandrel, hypotube, or inflated balloon into the interior of the stent to protect the inner surface. The outer surface of each stent was bead blasted, using bead diameters in the range of 10 µm to 50 µm. Stents #1 and #2 were bead blasted at 60 PSI pressure and stents #3 and #4 were bead blasted at 30 PSI pressure, as indicated in Table 1. Bead blasting was done at a distance of approximately 5 cm from the stent. The beads were passed very quickly, in approximately 1-3 seconds, down and up over the stent outer surface. The stent was then rotated 120° and the process repeated twice so the entire stent was roughened. After bead blasting, stents #1-#4 were cleaned by immersion in an ultrasonic isopropyl alcohol bath for 20 minutes and allowed to dry. Stent #5 was also cleaned in an ultrasonic isoproply alcohol bath for 20 minutes and allowed to dry. Uncoated stents #1-#5 were weighed.

A coating solution was made by adding EVOH (ethylene vinyl alcohol copolymer) to DMSO (dimethylsulfoxide) in a weight ratio of 1:4 EVOH:DMSO. Tetrahydrofuran (THF) was added to the EVOH:DMSO solution. Tetrahydrofuran constituted 20% by weight of the total weight of the solution. The solution was vortexed and placed in a tube. Stents #1-#5 were each dipped into the solution. The coated stents were passed over a hot plate, for about 3-5 seconds, with a temperature setting of about 60° C. The coated stents were cured in a convection oven at 60° C. for one hour. The coated stents were then re-dipped into the solution, passed again over the hot plate as above and cured in the convection oven at 60° C. for four hours. The coated stents were weighed and the weight difference between the coated and non-coated stents was calculated. The results are shown in Table 1 below. For the stents #1-#4 the amount of coating on the stent is greater than that of stent #5.

| Stent | Pressure Used in Bead Blast (PSI) | Weight difference between coated and uncoated stent (weight of coating) (mg) |
| --- | --- | --- |
| #1 | 60 | 0.187 |
| #2 | 60 | 0.160 |
| #3 | 30 | 0.168 |
| #4 | 30 | 0.158 |
| #5 | none | 0.090 |

To test the adherence of the coating, stents #1-#5 were expanded on a balloon and examined visually with a microscope. No peeling or defects in the stent coatings were observed.

While particular embodiments of the present invention have been shown and described, it will be clear to those of ordinary skill in the art that changes and modifications can be made without departing from this invention in its broader aspects and, therefore, the appended claims are to encompass within their scope all such changes and modifications as fall within the true spirit and scope of this invention.

What is claimed is:

1. A method for making an implantable medical device comprising:
   forming a patterned mask on a designated region of a surface of the implantable medical device, the patterned mask including openings to expose the surface of the implantable medical device;
   etching through the openings with an etchant to form asperities on the surface on the implantable medical device; and
   applying a layer of a coating material over the asperities, wherein at least some of the asperities extend out from the layer of the coating material,
   wherein the implantable medical device comprises a generally tubular structure having an inner surface and an outer surface.

2. The method of claim 1, wherein the outer surface is the surface on which the asperities are formed.

3. The method of claim 2, further comprising masking the inner surface while forming the asperities.

4. The method of claim 1, wherein the designated region comprises the entire outer surface of the implantable medical device.

5. The method of claim 1, wherein the coating material comprises a therapeutic substance.

6. A method for making an implantable medical device comprising:
   forming a patterned mask on a designated region of a surface of the implantable medical device, the patterned mask including openings to expose the surface of the implantable medical device;
   etching through the openings with an etchant to form asperities on the surface on the implantable medical device;
   applying a layer of a coating material over the asperities, wherein at least some of the asperities extend out from the layer of the coating material; and
   applying a second layer of a coating material to the implantable medical device or a portion thereof so as to cover at least a part of the layer of coating material.

7. The method of claim 6, wherein at least one of the layers comprises a therapeutic substance.

8. The method of claim 1, wherein the implantable medical device includes a plurality of depots in the surface.

9. The method of claim 8, further comprising depositing a material comprising a therapeutic substance into the depots and over the asperities.

10. A method for making an implantable medical device comprising:
    forming a patterned mask on a designated region of a surface of the implantable medical device, the patterned mask including openings to expose the surface of the implantable medical device;
    etching through the openings with an etchant to form asperities on the surface on the implantable medical device; and
    applying a layer of a coating material over the asperities, wherein at least some of the asperities extend out from the layer of the coating material, wherein the implantable medical device is a stent or a graft.

11. The method of claim 1, wherein the implantable medical device is made of a composite material including more than one component, and wherein at least one of the components can be dissolved by the etchant.

12. A method for making an implantable medical device comprising:
    forming a patterned mask on a designated region of a surface of the implantable medical device, the patterned mask including openings to expose the surface of the implantable medical device;
    etching through the openings with an etchant to form asperities on the surface on the implantable medical device, wherein the asperities include cavities, and wherein at least some of the cavities have a depth between 0.1 µm and 10 µm; and
    applying a layer of a coating material over the asperities, wherein at least some of the asperities extend out from the layer of the coating material.

13. A method for making an implantable medical device comprising:
    forming a patterned mask on a designated region of a surface of the implantable medical device, the patterned mask including openings to expose the surface of the implantable medical device;
    etching through the openings with an etchant to form asperities on the surface on the implantable medical device, wherein the surface including the asperities has a roughness factor between 50 nm and 5 µm; and
    applying a layer of a coating material over the asperities, wherein at least some of the asperities extend out from the layer of the coating material.

14. A method of manufacturing an implantable medical device, comprising:
    depositing a protective coating on a portion of an implantable medical device;
    exposing the device to an etchant to form asperities on a second portion of the implantable medical device not protected by the protective coating; and
    applying a layer of a coating material over the asperities, wherein at least some of the asperities extend out from the layer of the coating material,
    wherein the implantable medical device comprises a generally tubular structure having an inner surface and an outer surface.

15. The method of claim 14, wherein the protective coating includes a polymer.

16. The method of claim 14, wherein the protective coating is deposited on the inner surface.

17. The method of claim 14, wherein the implantable medical device is a stent or a graft.

* * * * *

Disclaimer 7,335,314 B2 — Steven Z. Wu, Santa Clara, CA (US); Sameer Harish, Fremont, CA (US); Deborra Sanders-Millare, San Jose, CA (US); Judy A. Guruwaiya, San Jose, CA (US); Daryush Mirzaee, Sunnyvale, CA (US); Syed Hossainy, Fremont, CA (US); Charlene Chen, Redondo Beach, CA (US). METHOD OF MAKING AN IMPLANTABLE MEDICAL DEVICE. Patent dated February 26, 2008. Disclaimer filed August 4, 2008, by the assignee, Advanced Cardiovascular Systems Inc.

The term of this patent shall not extend beyond the expiration date of Patent No. 6,805,898.

(*Official Gazette October 14, 2008*)